United States Patent [19]

Lee et al.

[11] Patent Number: 5,137,531
[45] Date of Patent: Aug. 11, 1992

[54] OUTSIDE PERFUSION TYPE BLOOD OXYGENATOR

[75] Inventors: Jeffrey A. Lee, New Hope; Louis C. Cosentino, Plymouth; Perry L. Blackshear, Mahtomedi; Daniel A. Baker, Minnetonka, all of Minn.

[73] Assignee: Minntech Corporation, Minneapolis, Minn.

[21] Appl. No.: 449,962

[22] PCT Filed: Jul. 28, 1987

[86] PCT No.: PCT/US87/01850
§ 371 Date: Jan. 23, 1990
§ 102(e) Date: Jan. 23, 1990

[51] Int. Cl.$^5$ ............................................. A61M 1/14
[52] U.S. Cl. ..................................... 422/46; 422/48; 128/DIG. 3; 261/DIG. 28; 210/321.79; 210/321.88
[58] Field of Search ............ 422/46, 48; 128/DIG. 3; 261/DIG. 28; 210/321.79, 321.88

[56] References Cited

U.S. PATENT DOCUMENTS

| | | | |
|---|---|---|---|
| 3,794,468 | 2/1974 | Leonard | 422/48 |
| 3,834,544 | 9/1974 | Tyson, Jr. et al. | 210/321.75 |
| 4,639,353 | 1/1987 | Takemura et al. | 128/DIG. 3 |
| 4,659,549 | 4/1987 | Hamada et al. | 128/DIG. 3 |
| 4,749,551 | 6/1988 | Borgione | 210/321.84 |
| 4,791,054 | 12/1988 | Hamada et al. | 422/46 |

Primary Examiner—Lynn M. Kummert
Attorney, Agent, or Firm—Vidas & Arrett

[57] ABSTRACT

A device having a blood oxygenator and heat exchanger of the outside perfusion type. The blood oxygenator employs a tightly packed, crisscrossing bundle of gas permeable hollow fibers. The heat exchanger employs a bundle of polyurethane, liquid impermeable hollow tubes. A center divider facilitates two separate compartments and allows control over pack densities within each compartment while allowing blood to move in a planar manner throughout the device.

21 Claims, 6 Drawing Sheets

OUTSIDE PERFUSION TYPE BLOOD OXYGENATOR

FIELD OF THE INVENTION

This invention relates to a blood oxygenator of the outside perfusion type using hollow-fiber membranes and to blood oxygenators having coextensive integral heat exchanging units.

DESCRIPTION OF THE PRIOR ART

Blood Oxygenator

In known blood oxygenators, hollow fibers are used as a means to bring blood into contact with oxygen and provide a means for removal of carbon dioxide from the blood. For simplicity, such gas exchange will be referred to herein with regards to the oxygenation only, it being understood that transfer of oxygen into and carbon dioxide out of the blood is taking place. The fibers are typically made of a homogeneous membrane of gas-permeable material such as silicone or of hollow fibers made of a microporous membrane of hydrophobic polymeric material such as polyolefins.

There are two types of hollow fiber blood oxygenators: the inside perfusion type in which blood is passed through the bores of the hollow fibers while oxygen is passed on the outside of the hollow fibers and the outside perfusion type. Blood oxygenators of the outside perfusion type pass oxygen through the bores of the hollow fibers while blood is flowed past the outside of the hollow fibers.

In blood oxygenators of the inside perfusion type, no channeling of the blood occurs provided the blood is uniformly distributed and fed to the interior of the large number of hollow fibers involved. However, since the blood flowing through the bores of the hollow fibers moves in a virtually perfect laminar flow, the internal diameter of the hollow fibers needs to be reduced to a small diameter in order to increase the oxygenation rate (i.e., the oxygen transfer rate per unit volume of blood per unit area of membrane).

The laminar flow phenomenon of the blood passing through the hollow fibers presents many problems even when very fine hollow fibers are used. The result is that the oxygenation rate of a blood oxygenator of the inside perfusion type is not as beneficial as might be expected. Effectiveness of oxygen transfer is in part determined by the surface area contact of the blood with hollow fiber. Obviously, a much larger surface area contact results when blood is on the outside of the hollow fiber than when the blood is internal to the fiber.

If the oxygen is not distributed uniformly into the blood, the carbon dioxide desorption rate from the blood (i.e., the carbon dioxide transfer rate out of the blood per unit volume of blood per unit area of membrane) will be reduced.

In the common configuration for inside perfusion blood oxygenators, a cylindrical housing is simply packed with a large number of hollow fibers for gas exchange arranged so that the hollow fibers are parallel to the longitudinal axis of the cylindrical housing. Blood oxygenators of this construction have lower than desired gas exchange rate per unit area of the hollow fiber membrane.

In contrast, in blood oxygenators of the outside perfusion type the oxygen can be distributed uniformly through the spaces between adjacent fibers and the blood can be expected to move with better mixing. However, outside perfusion has had the disadvantage of being subject to less than the desired oxygenation of the blood because of regional channeling of the blood as it passes transversely to the outsides of the hollow fibers.

The known outside perfusion type blood oxygenators in which the hollow fibers are in perpendicular orientation to the direction of blood flow produces more mixing of the blood as the blood flows than inside perfusion constructions. This arrangement can bring about an improvement in oxygenation rate, as compared with those inside perfusion types or construction in which the hollow fibers are arranged to have their length parallel to the direction of blood flow. However, if the number of fibers used in such a blood oxygenator is large (as is desirable) and/or the flow rate of blood is increased in order to treat large volumes of blood, problems arise. For example, unacceptable pressure drop of the blood between inlet and outlets and/or channeling of the blood between groups of fibers may occur. By channeling it is to be understood that a significant flow of blood takes place through relatively large area voids between fibers so that there is little or no mixing. As the rate of oxygen transfer primarily takes place in a thin boundary layer adjacent the hollow fibers, the effectiveness of desired oxygenation is reduced.

Blood-side convective mixing is essential for efficient gas transfer in blood oxygenators. Without such mixing, sharply defined boundary layers of fully oxygenated blood develop near the exchange surfaces and the fluxes of oxygen and carbon dioxide tend to be low. Low transport efficiency results in bulky devices with undesirably high blood priming volumes.

Other investigators have proposed constructions in attempts to reduce these problems. In U.S. to Takemura, Pat. No. 4,639,353, an oxygenator is shown in which a plurality of contact chambers are utilized each being limited in thickness as an attempt to discourage the undesired channeling.

Heat Exchanger

In prior art heat exchangers for blood oxygenator systems, the heat exchanger is typically made of a metal such as stainless steel tubing. Such materials are not as blood compatible as desired. Others have used polyethylene or polypropylene hollow fiber bundles in heat exchangers. However, potting compounds are less certain than is desired. It is mandatory that there be no leakage of the cooling fluid used in the heat exchanger to the blood. If water or other heat exchange medium were to leak into the blood being treated, the impact to the patient could be serious.

SUMMARY OF THE INVENTION

The present invention provides blood oxygenators of the outside perfusion type having high oxygen transfer rates, high carbon dioxide transfer rates, efficient heat exchange, and a construction which results in little or no stagnation of blood. Channeling of the blood is minimized. The devices of the invention provide very good oxygenation performance. As compared to prior devices having equal fiber surface area, the devices of the present invention provide superior oxygenation. Thus, a desired oxygenation rate may be achieved while using less total quantities of the costly fibers.

When coupled with the heat exchanger of the invention, the unitary device results in a highly compact blood oxygenator capable of giving the needed gas transfer and temperature control. A further advantage of the construction of the invention lies in the parallel plane construction of the oxygenator and heat exchanger sections coupled with a means to have an uninterrupted, substantially planar flow pattern of blood transverse to both the oxygenator and heat exchanger without an interruption.

The heat exchanger is of an outside perfusion type construction utilizing a bundle of polyurethane hollow tubes. The large surface area provided for contact with the blood provides a very effective heat exchanger of the compact size even though polyurethane tube have a low heat transfer coefficient compared to stainless steel. Polyurethane hollow tubes, unlike the polyolefin heat exchange fiber materials previously used, are completely compatible with urethane potting compounds used to encapsulate the ends of both the oxygenator hollow fibers and of the heat exchanger hollow tubes. Therefore, the heat exchanger built in accordance with this invention substantially removes the possibility of leakage at the hollow fiber and hollow tube end potting interface. Such a possibility of leakage exists in the prior art.

The combination of oxygenator and heat exchanger provides an oxygenator which, as designed, meets the Draft Standard For Blood/Gas Exchange Devices (Oxygenators) of the Association for the Advancement of Medical Instrumentation, Feb. 1982 Revision. (Commonly referred to in the industry as the A.A.M.I. Standards).

The devices of the invention are arranged and designed to be relatively simple to construct, thereby lowering costs of manufacture over known prior art units.

According to the present invention, there is provided a device comprising a blood oxygenator and an integral heat exchanger. A housing divider-diffuser plate with perforations separates the blood oxygenator hollow fiber bundle from the heat exchange hollow tube bundle. Access means are provided so that blood enters the heat exchanger section through a port which opens into a first chamber extending coextensive with the length and width of the heat exchange hollow tube bundle. Blood entering the first chamber passes through a first perforated diffuser plate which acts to distribute blood evenly over the surface of the heat exchange hollow tubes and across the depth of the bundle of tubes.

The heated or cooled blood is then distributed, without being recollected to a bulk quantity, to an oxygenator bundle of hollow fibers by passage through the housing divider diffuser plate. The oxygenator bundle of hollow fibers consists of tightly packed hollow fibers. The fiber and the tube ends are all potted in potting compound in a single step at each end such that each fiber and tube extends between end potting blocks. Strong mixing of the blood is induced on fibers by the tortuous path that the blood must take in flowing past the fibers of the bundle.

The hollow fibers are laid into the device such that the fibers cross over each immediately previously laid adjacent fiber at an angle of between about 8 and about 25 degrees. At the completion of laying down one full layer of fibers across the housing-divider diffuser plate, the pattern of laying down is shifted slightly out of phase such that the next layer of fibers cross the previously laid fibers adjacent fibers at an 8 to 25 degree angle but are shifted from the underlying layer. This creates a relatively even pack density throughout the bundle, increases the tortuous blood path and virtually eliminates areas where shunting and channeling may occur.

Each fiber crosses over the next at an angle of from about 4 to about 13 degrees from the longitudinal axis of the core. The preferred angling of the fibers is at angles of about 9° from the sides of the housing. A pack density of about 50-55% of the available cross-sectional area at the midpoint has been found to minimize channeling and shunting without causing an unacceptable pressure drop. A lower packing density may be used within the potted ends of the fibers to facilitate fiber end encapsulation. A substantial drop in oxygen transfer is observed at a density of 45%. Channeling of blood flow is found in devices packed at less than about 40%. When the pack density is greater than about 55% the blood pressure drop between entering and leaving rises to unacceptable levels.

Blood, after traversing the oxygenation fibers, exits the oxygenating bundle through a second perforated diffuser plate while retaining its generally planar flow. The blood then passes out of the housing through an outlet which may open transversely to the length of the oxygenator fibers. Both of the perforated diffuser plates are spaced from the exterior housing and provide support to the fiber and heat exchanger bundles.

The required packing density of the oxygenator fibers and heat exchange tubes may be easily maintained by virtue of the three diffuser plates. The diffuser plates with the chamber and cover define a predetermined rigid cross-sectional area for the fibers and tubes.

The device is very compact which is an important feature of efficient oxygenators. The compactness may be achieved with a minimum of parts and manufacturing steps.

BRIEF DESCRIPTION OF THE DRAWINGS

The detailed description of the invention, including its preferred embodiment, is hereinafter described with specific reference being made to the drawings in which.

DETAILED DESCRIPTION OF THE INVENTION

Figure 1:
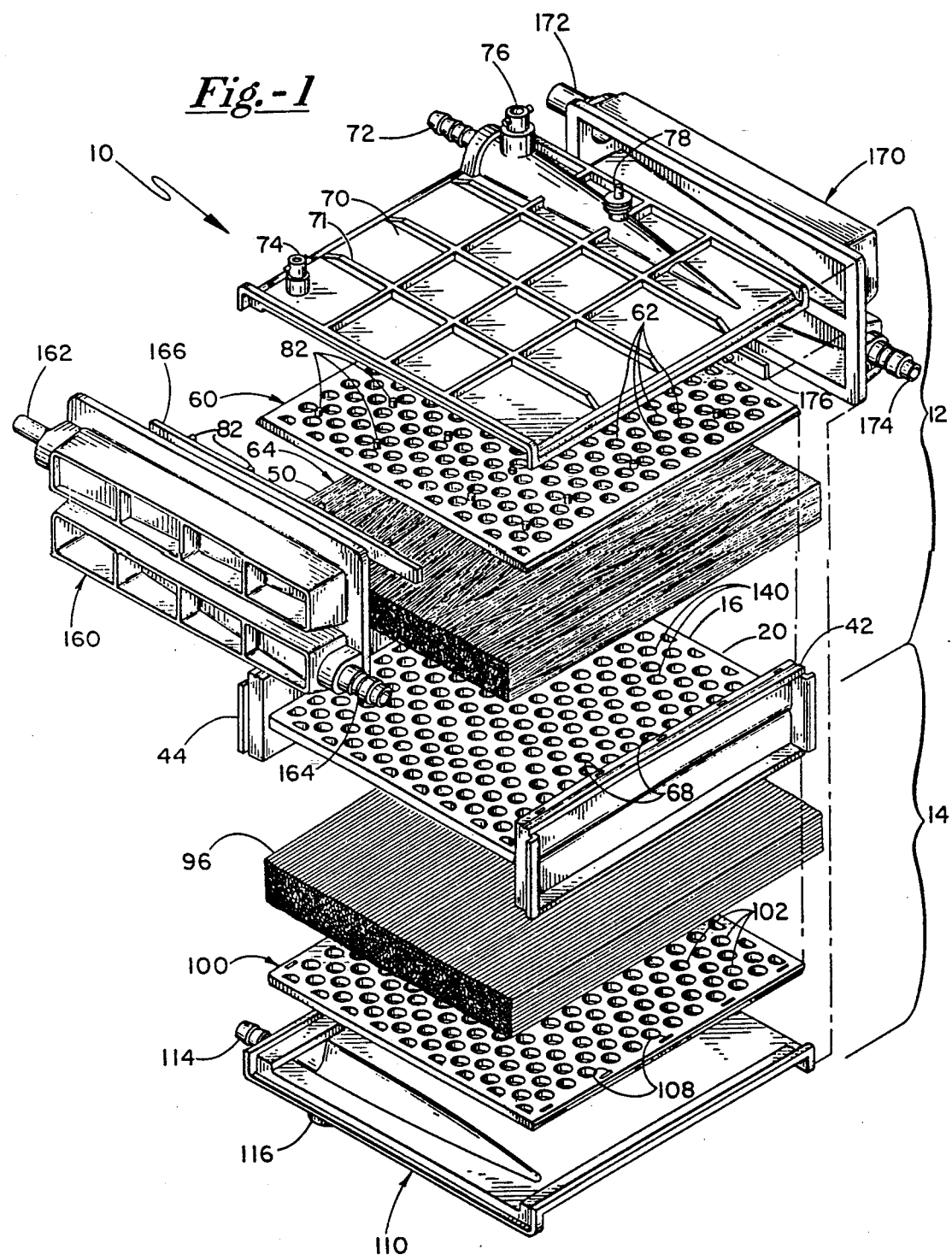
FIG. 1 is an exploded pictorial view of the device of the invention.

The device generally marked 10 of FIGS. 1—6 comprises an oxygenation section 12 and a heat exchanger section 14 which are separated by a common center divider 16. Preferably, the casing and divider elements are formed from biocompatible plastics capable of hermetically being bonded by potting compounds of the urethane type.

Device 10 includes an elongated rigid core member 20 of generally H-shaped cross-section which defines an upper channel shaped region 30 and lower channel shaped region 40. Each channel region is a longitudinally extending groove in the core member. Center divider 16 forms the web between the outside legs 42, 44 of the H of the core member 20.

Oxygenator section 12 includes the area defined by upper channel 30. Channel 30 is filled with hollow fibers 50 arranged longitudinally such that the hollow fibers generally are oriented in the direction roughly parallel to the legs 42, 44.

Each of the hollow fibers 50 is a membrane designed for gas exchange. Each hollow fiber may comprise a porous resin capable of gas transfer such as polypropylene, polyethylene or other biocompatible suitable material which provides a gas exchange. The fibers are liquid impermeable. Suitable fibers for this purpose are well known and commercially available from a number of vendors including Mitsubishi Rayon Co., Ltd. of Tokyo, Japan and Celanese Chemical Co. of New York, NY.

Figure 3:
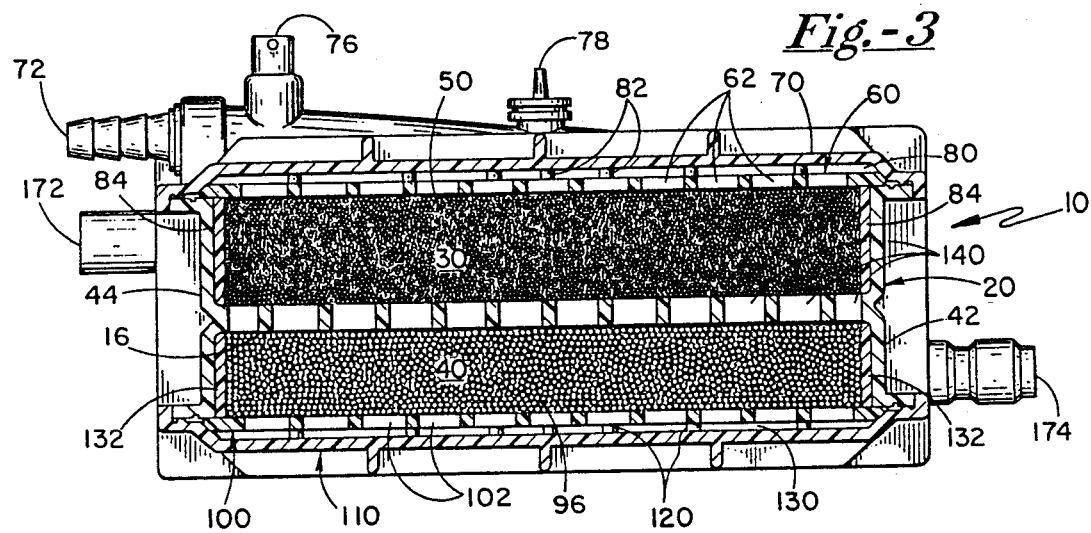
FIG. 3 is a cross-section taken along line 3—3 of FIG. 2.
Figure 4:
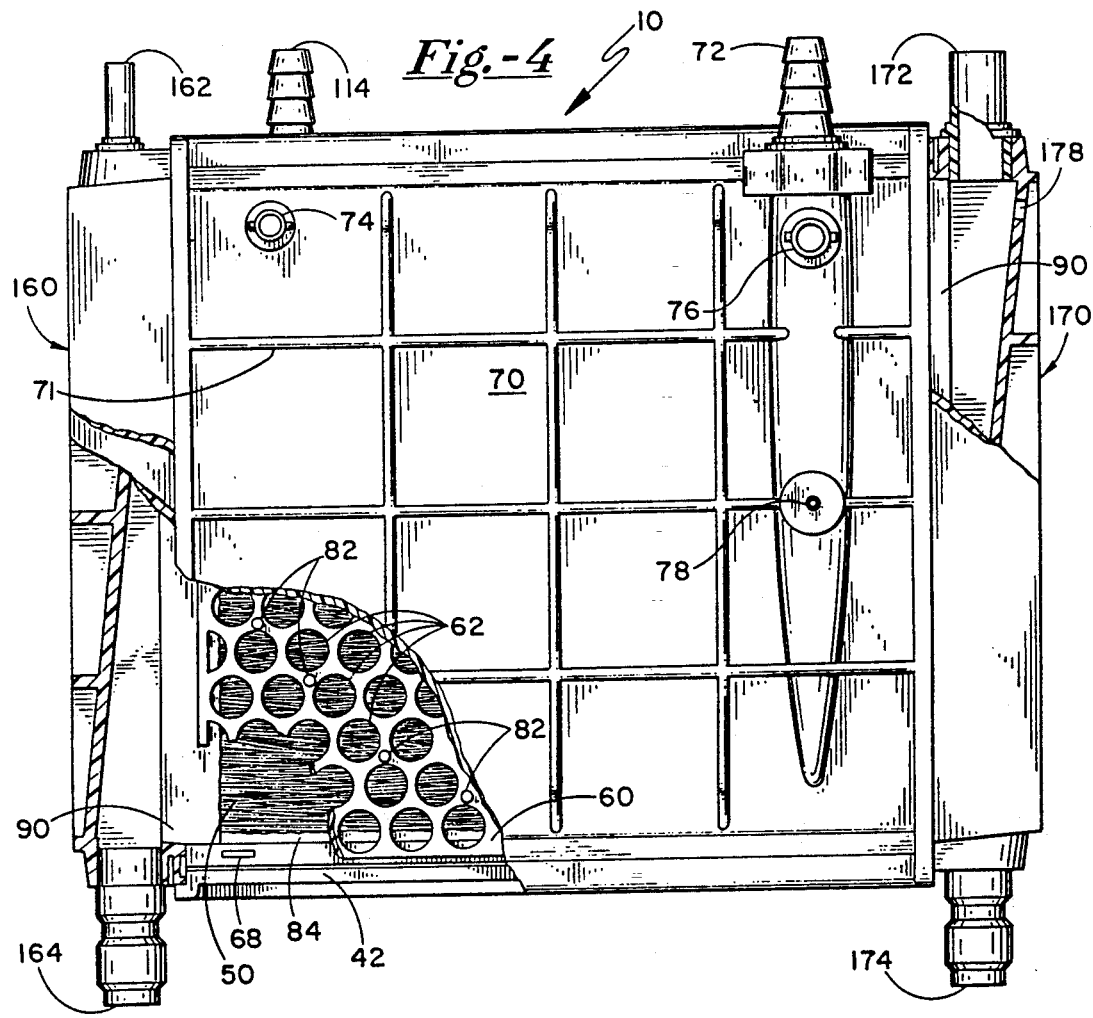
FIG. 4 is a top plan view of the device of FIG. 2 with portions cut away to show the oxygenator fibers and diffuser plate.
Figure 5:
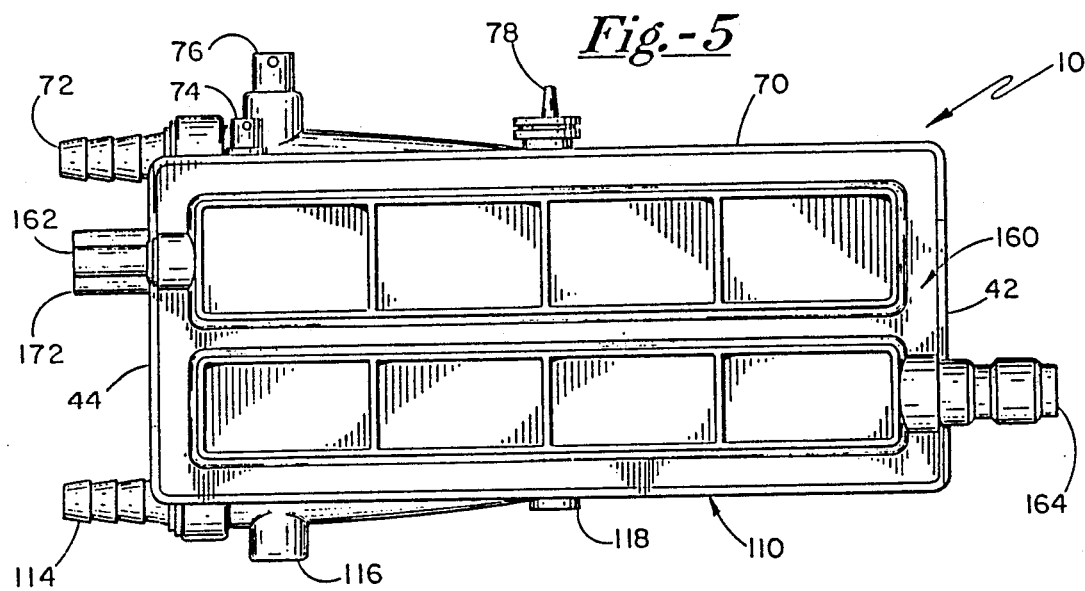
FIG. 5 is a side plan of the device of FIG. 2.
Figure 6:
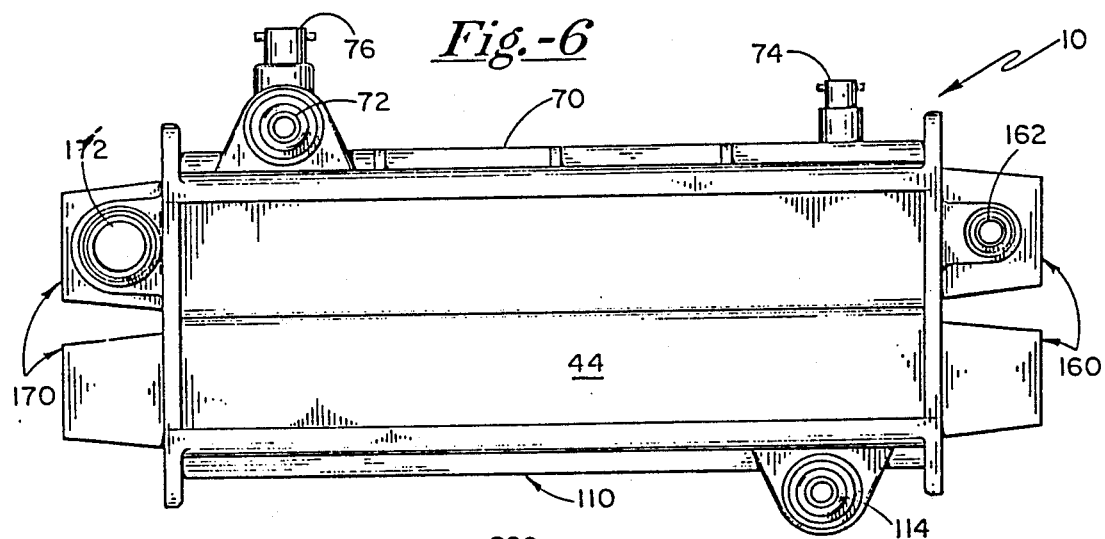
FIG. 6 is a front plan view of the device of FIG. 2.

A diffuser plate 60 as shown in FIGS. 1, 3, and 4 covers the upper layer of hollow fibers 50 and is attached to legs 42, 44 along its side edges. Diffuser plate 60 includes a plurality of orifices 62 which are spaced throughout the plate 60. Orifices 62 allow the passage of blood through plate 60 from within the upper channel shaped region 30. The plates adjacent the fibers are constructed such that each orifice border is chamfered to minimize sharp edges which might damage the hollow fibers.

The diffuser plate 60 bears against the hollow fiber bundle 64 within upper channel 30. The plate 60 assists in holding the hollow fibers at the desired pack density of fibers per unit area within the region 30. It is assisted in that purpose by cover 70. The orifices in plate 60 allow blood to pass through the bundle 64 from the plate 20 in a substantially planar manner. This provides optimum exposure of the blood to fiber surfaces and minimizes the pressure drop across the unit. It also aids in eliminating potential areas of stagnation which decreases efficiency and might give rise to clotting.

Orifices 62 (and 102, 140 described below) are preferably no greater than ½ inches (1.27 cm) and preferably about ⅜ inches in diameter. Larger diameter orifices reduce the ability of the plate to provide pack density control and will allow the fibers to bulge into the orifices thereby potentially creating void spots in the fiber bundle therebelow. Another disadvantage in fibers bulging into the orifices is that pinching to close a fiber might occur.

An advantage in providing large diameter orifices of the preferred size is that the amount of plate surface area blocking fibers from gas exchange is reduced. By minimizing such fiberplate contact area the overall efficiency of the device is improved. The number of orifices should, therefore, be maximized at the preferred size so long as the outlet plate and cover 70 remains sufficiently rigid to provide pack density control.

Figure 2:
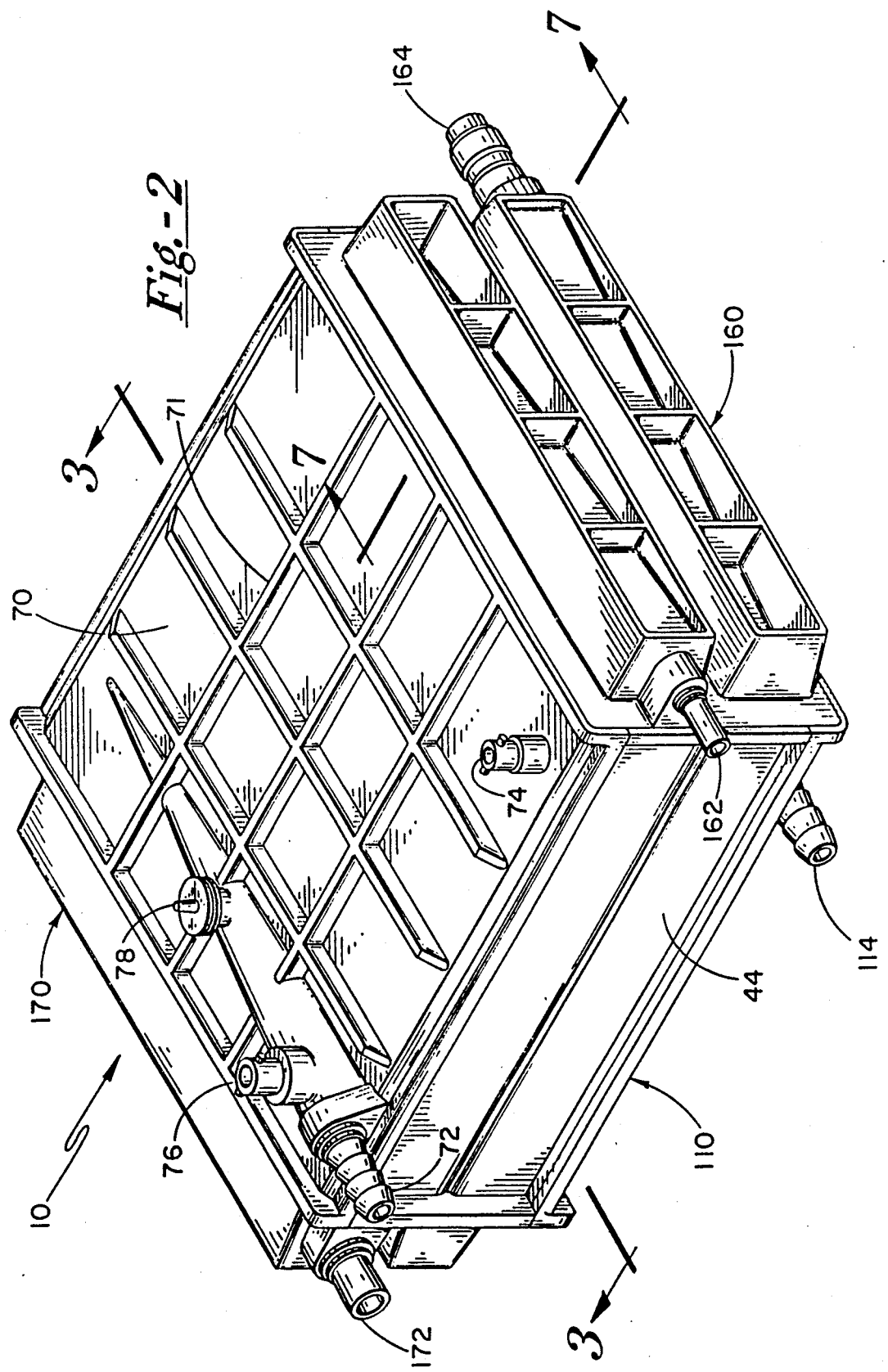
FIG. 2 is a perspective view of the unexploded device of FIG. 1 from the reverse side.

An outer cover member 70 further encloses the hollow fiber bundle as shown in FIGS. 1, 2, and 4. Cover 70 includes a blood outlet port 72 which preferably extends perpendicularly to the fibers across substantially the entire bundle as shown. Preferably, cover 70 also includes a vent port 74, temperature probe port 76 and a sample port 78. Sample port 78 may include a check valve/breather valve which allows a sample to be withdrawn without introducing air into chamber 80. As shown, cover member 70 defines a chamber 80 above diffuser plate 60. The spacing between outer cover 70 and diffuser plate 60 is provided for by spacer nodes 82 and maintained in part due to the rigidity of diffuser plate 60. However, the force of maintaining the pack density of the fibers toward the diffuser plate tends to deform the highly perforated plate toward the cover. Therefore, a plurality of spacer nodes 82 are provided between the cover and outer plate as shown in FIGS. 1 and 3 to further stiffen diffuser plate 60 so as to maintain pack density while providing superior diffusion. Cover 70 is preferably provided with a grid of outer ribs to give it greater rigidity, as shown in the FIGS. Because of blood pressure there is a tendency for Cover 70 and plate 60 to bow and thereby reduce packing density. Ribs 71 remove this tendency.

The packing density of hollow fiber bundle 64 is specified by the following formula:
packing density =

$$P (\%) = (d/2)^2 N / ab \times 100$$

Where "d" represents the outer diameter of the hollow fibers, "n" the number of hollow fibers enclosed within the housing, "a" the inner width of the housing and "b" the inner height of the housing between the diffuser plate 60 and center divider 16.

The preferred packing density is between about 50 and 55%. Pack densities below about 45% at this winding angle show a substantial drop in performance and densities as low as 40% will result in channeling of blood. Pack densities of only 40% at this winding angle often exhibited visible channels through which blood is preferentially shunted. Such shunting prevents that blood from being fully oxygenated and carbon dioxide removal is also decreased. If shunting is of a significant portion of the blood, stagnation of the slower flowing blood is more likely. The preferred pack density described above will change with differences of fiber diameter and winding angle. This will be readily determined empirically by testing the angle of winding for pack density of various size fibers.

Figure 8:
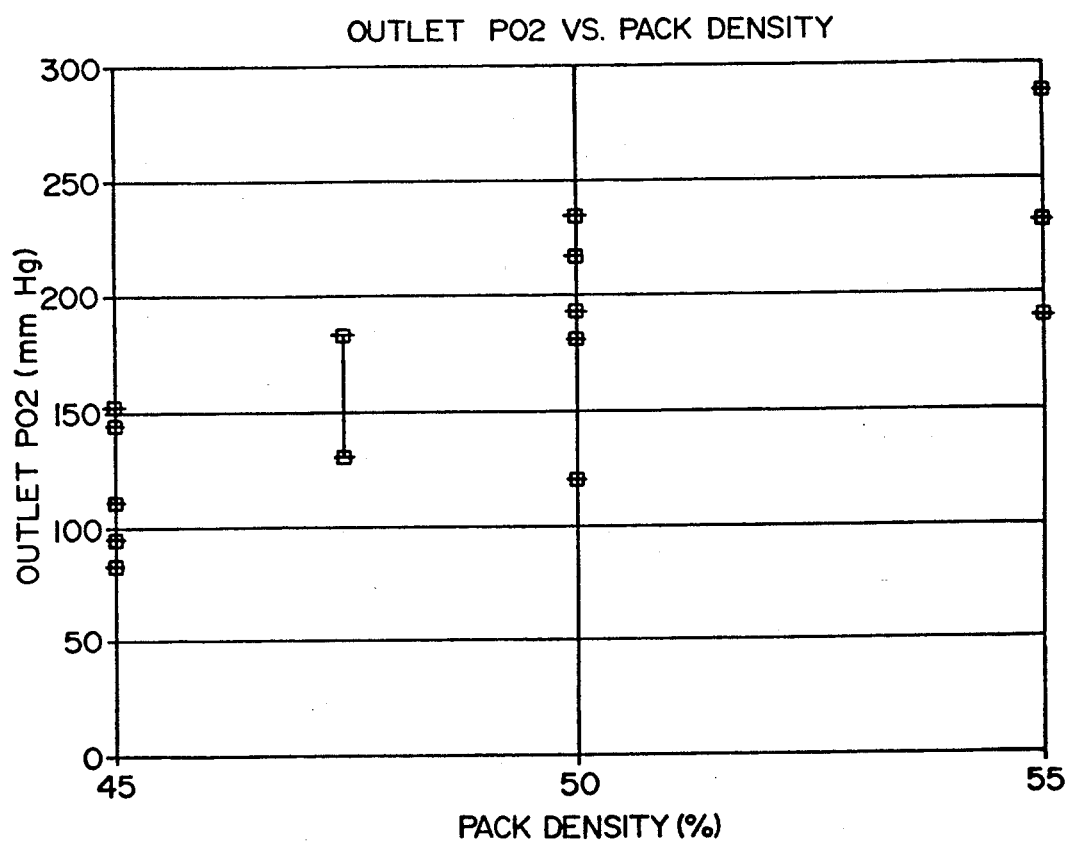
FIG. 8 is a graph showing the relationship of fiber pack density to outlet partial pressure of oxygen in the blood oxygenator of the invention.

As shown in FIG. 8 entitled "Outlet pO2 vs. Pack Density," in order to obtain a blood outlet oxygen partial pressure of at least 200 mm Hg the pack density should be between about 50 and 55 percent. These results are for fibers and winding angles described above.

Figure 9:
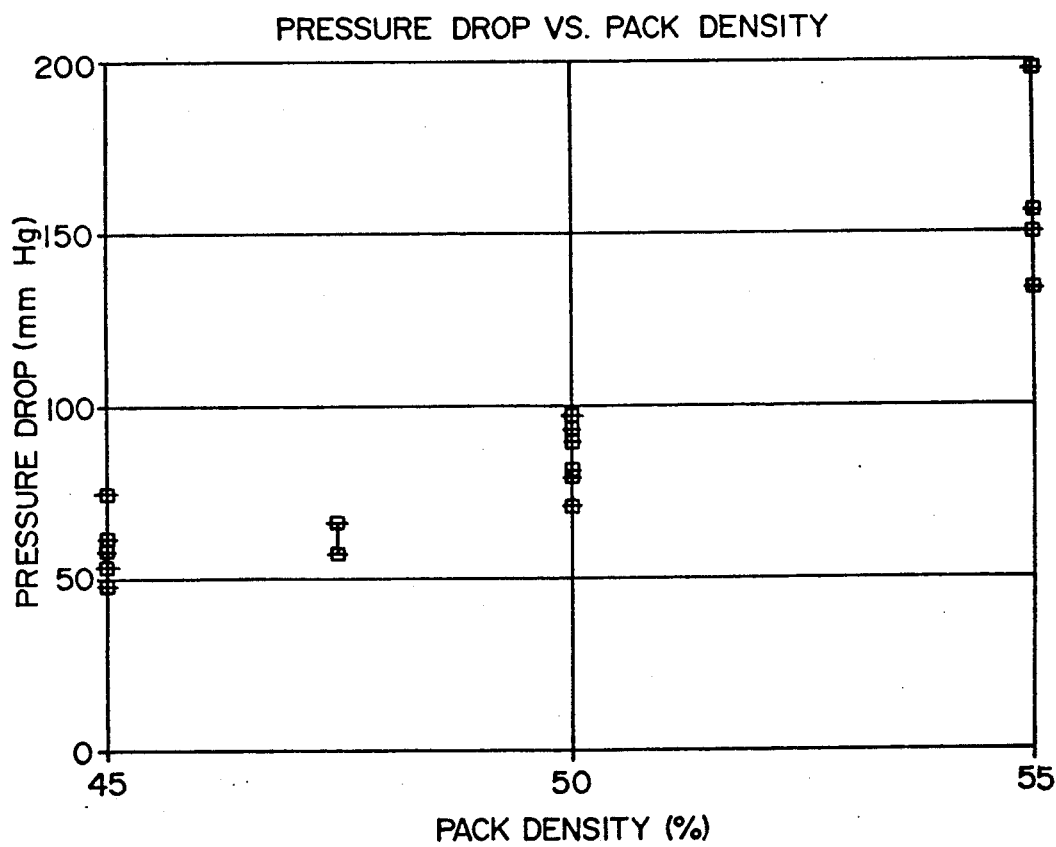
FIG. 9 is a graph showing the relationship of pressure drop to fiber pack density through the oxygenator fiber bundle.

FIG. 9, entitled "Pressure Drop vs. Pack Density," shows that the pressure drop through the oxygenator bundle at a pack density between 50 and 55 percent is less than 150 mm Hg. Again these results are for fibers and winding angles as described above.

The hollow fibers within the oxygenator section are preferably laid in single fiber or in groups of fibers such that successive single fiber or group of fibers are laid at an angle to the previous fiber or group of fibers. After one complete layer is laid into upper channel 30, the pattern is shifted slightly. Each successive layer is laid such that the fibers within the layer cross each other as above. Each layer is slightly shifted in phase from the next. The overall effect is that a very uniform pack density is possible and channels are eliminated. The crossing fiber arrangement is preferable over parallel fiber packing since it forces the blood into effective, but gentle, transverse mixing without traumatizing the blood. Straight, uncrossed fibers packed to a 50-55% density may result in some shunting of blood and provide less mixing and therefore, less oxygen transfer.

One method of obtaining the preferred criss-crossing arrangement of fibers is to wind fibers into the oxygenator section of a plurality of cores 20 which are arranged around the periphery of a polygonal wheel. For example, such apparatus and procedures are described in U.S. Pat. No. 4,267,630, 4,276,687, 4,341,005 and 4,343,668. A reciprocating fiber guide assembly controls the angle that the fibers are laid into the cores while the wheel rotates. An optimum angle is about 9° measured between the fiber and edge of a core leg 42 or 44. Steeper angles create lower pack densities. Lower angles create higher pack densities.

During the winding process it is desirable to maintain an "as wound" pack density close to the desired finished pack density. Winding the fibers at a density substantially less than the finished density allows the fibers to move so that the center will have significant amount of undesired air space creating channels. Winding fibers in at a higher pack density than the finished density can create a void space between the top layer of fibers and the diffuser plate 60. As the bundles are removed from the winding wheel, the fibers can randomly move to fill the void space, again jeopardizing the precise spacings of the fiber layers.

The oxygenator diffuser plate 60 is then placed on top of the core and the fibers are cut with a knife. The perforated plate 60 is tacked onto legs 40, 42 such as by ultrasonic weld points 68. Plate 60 thereby holds the pack density at the desired value while allowing fluid to flow in the planar manner described previously. The fiber ends may be melted shut or otherwise sealed prior to end potting. The cores are then removed from the wheel for assembly of the outer jackets.

The currently preferred method is to wind the fibers onto a hexagonal wheel to which six cores 20 are attached such that the upper channel 30 may receive fiber windings. The actuator has a linear speed of 7.2432 inches per second and the wheel has a rotational speed of 50.25 rpm. The linear acceleration at reciprocating points is 147 inches per second. The winding width of upper channel 30 is 5.75 inches and the angle between fibers is 18.30 degrees. Each layer consists of 184 turns of the wheel. A 0.020 second linear actuator pause is made between each layer to slightly offset each layer.

After the required number of winds have been made, a side potting compound 84 is introduced along the contact of the hollow fibers and the face of legs 42, 44 of the core 20. Due to the winding angles employed, the packing density at the center of the contact face tends to be lower than desired and channeling is possible. Therefore, a urethane potting compound is introduced as a bead projecting several fibers deep along the contact edge to eliminate possible channels. An acceptable urethane side potting compound is available from Caschem, Inc. of Bayonne, N.J. and has a viscosity of about 90,000 cps, marketed as Vorite®689 and Polycin®943.

Following winding, the oxygenator diffuser plate 60 is placed on top of the core and tack "welded" to legs 40, 42 by ultrasonic welding. Then the fibers are cut with a knife. Diffuser plate 60 thereby maintains the pack density near or at the desired value. The cores are then removed from the wheel for assembly of the outer jackets. The fiber ends may be melted shut or otherwise sealed prior to end potting.

The outer cover 70 is sealed onto the core. Ribs 71 will aid in pressing the fibers to the ultimately desired packing density. The hollow fiber bundle 64 will ultimately be centrifugally end potted, as will be described below along with the heat exchanger tubes. The end potting region is shown in the drawings as reference numeral 90. Because of the high packing density, the ends of the fibers are preferably spread out manually prior to potting to ensure that each fiber is encased within the compound, this, of course, gives a reduction in packing density within the potting compound region.

The heat exchange section 14 includes the region defined by lower channel 40. Channel 40 is filled with a plurality of substantially parallel, liquid impermeable hollow tubes 96. The heat exchange hollow tubes 96 are preferably formed from a polyurethane resin such as B.F. Goodrich Estane ™ 58091. The tubes are much larger than the hollow fibers in the oxygenator, typically being about 0.033 inches (840 microns) in outside diameter with a wall thickness of about 0.004 inches (102 microns). In contrast, a typical oxygenator fiber has an outside diameter of about 200-450 microns and a wall thickness of less than 50 microns. The formation of heat exchanger tubes from polyurethane rather than the stainless steel, polyethylene, or polypropylene previously used represents a significant advance. While the efficiency of the heat exchanger is an important design consideration, it is vital that there must be no leakage. The end seals where polyurethane potting compounds are used with stainless steel tubes represent potential leakage areas of the cooling fluid into the blood.

The use of polyurethane heat exchange tubes with the polyurethane end potting compounds provides a positive seal which insures that no leakage will occur. This compatibility with the potting compound greatly increases the safety of the product.

The hollow tubes are packed into channel 40 such that channeling is minimized. However, performance of the heat exchanger is not greatly affected if some channeling is present. A pack density of between about 40% and 60% provides an efficient heat exchanger with an acceptable pressure drop. It is preferred to pack the polyurethane tubes at about a 45-55% pack density which provides an efficient unit, low pressure drop and low blood priming volume. The thin walled polyurethane hollow tubes provide good heat transfer. The efficiency desired is in ensuring that all of the blood is heated or cooled as desired, not in how much heat exchange fluid is required. The temperature differential between the blood and heat exchange fluid should be low to provide better control.

The heat exchanger tubes are preferably cut and then placed into the channel rather than wound into the channel. Winding is less preferable as it tends to cause the hollow tubes to bend may cause cracks or breaks. Additionally, the curvature may allow some tubes ends to be too far inward after cutting which during end potting which may result in leakage in the device. The hollow tubes are then preferably melted shut at both ends simultaneously into a bundle or may be dipped in wax to close the tubes for end potting. Currently, it is preferred to introduce side potting compound 132 along the interface of the heat exchanger tubes 96 with legs 42,44 as shown. Side potting 132 may extend several tubes deep into the heat exchange bundle and decreases the likelihood of channeling within the heat exchanger.

A diffuser plate 100 is preferably attached to the core 20 along legs 42, 44 as shown by ultrasonic welding at points 108. Diffuser plate 100 includes a plurality of orifices 102 and may be identical to the diffuser plate 60. A cover 110 (preferably ribbed for rigidity) further encloses the heat exchanger bundle as shown in Figs. 1, 3, 5 and 6. Cover 110 includes a blood inlet port 114 and may include a temperature probe port 116 and sample port 118.

Although the heat exchanger described above will function adequately without the diffuser plate, the addition of the diffuser plate 100 lessens shunting and better maintains the desired pack density of the heat exchanger tubes. This increases the efficiency of the heat exchanger. As in the case of the oxygenator diffuser 60, the heat exchanger diffuser 100 is preferably separated from cover 110 by a plurality of nodes 120. Nodes 120 may be joined to cover 110 and diffuser 100 thereby defining a chamber 130 therebetween.

Centrifugal end potting is well known in the art and is, for example, shown in U.S. Pat. No. 4,389,363 to Molthop. Suitable potting compounds are available from Caschem, Inc. of Bayonne, N.J. A polyurethane casting system of Caschem, Inc. is described in U.S. Reissue Pat. 31,389. After potting, the hollow fibers are reopened by conventional techniques such as by slicing through the potted bundle with a sharp knife to expose the interior of the fibers.

The heat exchanger and previously assembled oxygenator bundle may then be end potted at each end with a polyurethane potting compound. The hollow tubes are reopened after potting such as by cutting with a sharp knife. The end potting 135 provides a superior seal which provides maximum assurance that the seal will not leak.

Figure 7:
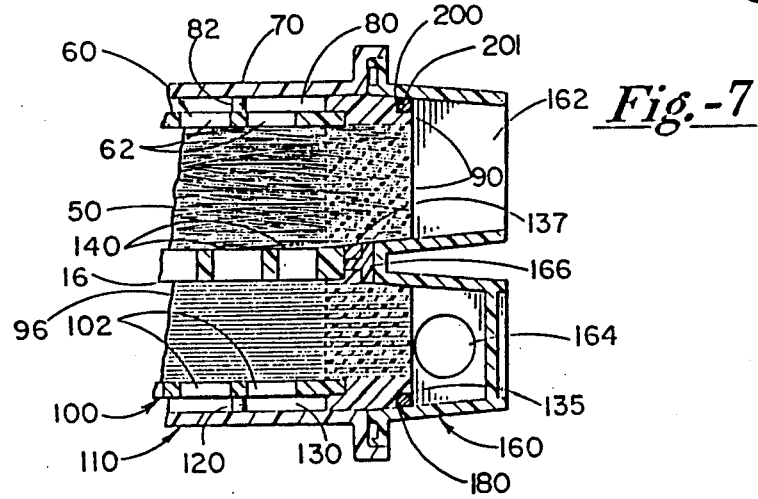
FIG. 7 is a partial cross-section taken along line 7—7 of FIG. 2.

The core 20 allows the end potting of the heat exchange tubes 96 and the oxygenator fibers 50 to be completed together in one potting. End potting tends to be time consuming and eliminating the need for two separate end potting procedures represents a very marked improvement. Also, a single step potting reduces the possibility of leakage around the potting edges. As shown in FIG. 7, the end potting 90 of the oxygenator bundle and the end potting 135 of the heat exchanger tubes 96 in one step results in a polyurethane dam 137 coextensive with potting 90 and 135. This dam 137 isolates the fibers 50 from the tubes 96 and encapsulates the end 10 divider plate 16. It has been found that dam 137 prevents the possibility of leakage which might otherwise occur in the absence of a dam extending in a contiguous manner between the center divider and the separate end potting areas.

As shown in FIGS. 1–5, blood outlet port 72 and blood inlet port 114 preferably are constructed and arranged such that blood is directed across substantially the width of the fiber and tube bundles in the respective chambers.

As shown in FIGS. 1 and 3, blood flows from the heat exchanger section into the oxygenator section by passing through perforations 140 in center divider 16. Center divider 16 is preferably constructed and arranged as described above for diffuser plate 60 and the same considerations apply as to the number and size of perforations 140. All three diffuser/dividers preferably have about 62% of their surface area removed in the form of perforations.

After the heat exchanger tube bundle and oxygenator hollow fiber bundle have been end potted and reopened, the device is completed by attaching end caps 160 and 170. Ends caps 160, 170 provide gas and heat exchange media inlets and outlets to the open ends of the hollow fiber and tube bundles.

End cap 160 is secured to perimeter of the cross-sectional end of core 20 and to outer jackets 70 and 110 and plastic strip 166. Plastic strip 166 has projecting lugs 167 which aid in spacing and the forming of dam 137. Alternate construction will have strip 166 formed as an integral part of center divider 16. In the preferred form in which a dam 137 is formed during the single end potting step, a seal is formed between a plastic strip 166 which is adhered to dam 137 along the width of the end potted region caps. A gas inlet 162 of end cap 160 allows gas to contact all of the open oxygenator hollow fiber ends. A heat exchange outlet 164 allows heat exchange media leaving the interior of the heat exchanger hollow tubes to exit the device.

End cap 170 is constructed in a similar manner to end cap 160. End cap 170 includes a gas outlet 172 which collects gas leaving the open ends of the oxygenator hollow fibers such that gas is exhausted through gas outlet 172. Outlet 172 is preferably sized to accept either a $\frac{1}{2}"$(1.27 cm) I.D. tubing set or a $\frac{1}{4}"$(0.63 cm) I.D. tubing set inserted into the lumen of outlet 172. Vent port 178 may also be provided as shown. Port 172 may be connected to a vacuum source in order to prevent anesthesia gas from escaping into the operating room. A heat exchanger inlet 174 provides heat exchange media to each of the heat exchanger hollow tubes through their open ends. As in end cap 160, end cap 170 may be sealed to plastic strip 166 such that the open ends of the heat exchanger hollow tubes are isolated from the open ends of the oxygenator hollow fibers.

One may achieve even greater assurance against the possibility of leakage between the spaces that are desired communication with open ends of the tube bundle and the open ends of the hollow fiber bundle and other undesired regions in the following manner. During the end potting of the hollow fibers and heat exchange tubes, a mold is used, configured to shape the perimeter region of the potting compound 90 and 35 to a shoulder 200 around the outer ends of hollow fiber bundle 64 and around the outer ends of hollow tube bundle 96. This is illustrated in FIG. 7. Prior to placing end cap 160 as a closure, O-rings 201 are placed onto shoulder 200. The tapered walls of end cap 160 press against O-rings 201 and effectively seal the space communication respectively with the interior of hollow fibers 50 and tubes 96 from each other as well as sealing the blood flow regions from either the gas passing through hollow fibers 50 or from the fluid used for heat exchange.

Of course, the seals described previously of the potting compound 90 and 35 also prevent undesired leakage.

Blood entering inlet 114 sweeps through chamber 130 and more uniformly contacts the heat exchanger bundle after passing through the diffuser 100. Chamber 130, in conjunction with diffuser 100 provides excellent blood flow distribution to the heat exchanger tubes. Observation of the blood through the outer jacket shows that it swirls in the chamber 130.

The oxygenator construction described above provides an even resistance to blood flow throughout the oxygenator section 12. Flow vectors are substantially equal throughout the fiber bundle 64 which maximizes oxygen transfer by minimizing shunting. The inventive outside perfusion design provides a greater surface area for gas transfer and provides better mixing. With the invention, it is possible by the mixing action of the blood in flowing around the fibers to get more red blood cells closer to blood plasma adhering to the fibers such that oxygen dissolved in the plasma may reach individual the red blood cells.

At the Association Advancement Medical Instrumentation (AAMI) Standard condition (blood flow rate =6L/min., inlet gas =100% O$_2$, venous hemoglobin saturation =65%, hemoglobin concentration =12 gm%) modified to a hemoglobin saturation =55%, a unit having only 3.8 square meters of hollow fiber surface area provides oxygen transfer at 450 ml/minute. Utilization of the fibers is maximized while pressure drop and blood prime volumes are kept at low values.

The design allows the mass production of oxygenators having excellent gas transfer rates with reduced production costs. The heat transfer efficiency is well within the recommendations of the AAMI Standards.

Through the use of the unique oxygenation section design, it is possible to maximize utilization of hollow fibers while minimizing the surface area of the hollow fibers. Since hollow fiber stock is expensive, the cost savings alone is an important advantage of the invention. The lower overall surface area of fibers also decreases the likelihood of platelet and fibrinogen aggregation on the fiber surface. A lower hemolysis rate is also found with the decrease in fiber surface area.

The case, diffuser plates, outer jackets and end caps are all preferably formed from a non-toxic, biocompatible plastic polycarbonate resins. Suitable for the purpose are the Lexan brand ® resins of General Electric Co. Polymers Product Department of Pittsfield, Massachusetts. Lexan ® 144 grade polycarbonate resins are currently preferred.

Oxygenators

If heat exchange is not needed in an integrated unit, the oxygenator features of the invention may be utilized by providing a core having a U-shaped cross-section. Center divider 16 becomes a replacement for diffuser plate 100 and is supported in spaced relationship to the outer case by projection. The outer jacket would then be secured to the center divider. Of course, the end caps would only need gas inlets and outlets. The oxygenator thus described provides all of the advantages found in the oxygenator section of the device. It may be used in conjunction with systems having their own separate heat exchange units if desired.

Heat Exchanger

The heat exchanger section described above for the device may be produced without an oxygenating section. A heat exchanger may be constructed by utilizing a core having a U-shaped cross-section such that center divider 16 is enclosed within outer jacket 70. As above, the end caps would be modified, in this case to provide heat exchanger inlets and outlets only.

Any application needing heat exchange with the advantages of using the polyurethane hollow tubes described above may be satisfied by following the teachings of the invention. A bundle of polyurethane hollow tubes may be placed in a case and end potted with a polyurethane end potting compound. After end caps are secured a heat exchanger is formed in which the interior of the hollow tubes are isolated from the flow paths along the outside of the tubes. Heat exchange media may be passed through the lumens or outside the lumens as desired by the application. The heat exchanger may include diffuser plates to increase the distribution of fluid over the tubes. The unique combination of polyurethane hollow tubes with the polyurethane end potting compound provides maximal security that there will not be leakage in the device.

Although the device is shown in the figures with a core having an H-shaped cross-section, the advantages of the invention may also be attained with a device in which the heat exchange tubes are generally perpendicular to rather than parallel to the oxygenator fibers. Such a device may be made by moving the lower portions of legs 42, 44 below the center divider to the other edges of the center divider. In such a construction the end caps would need to be separate and two separate end pottings would be required. A somewhat less efficient method of assembly would result.

In considering the invention it must be remembered that the disclosure is illustrative only and that the scope of the invention is to be determined by the appended claims.

What is claimed is:

1. A device comprising:
   a) a housing including an elongated rigid core of generally H-shaped cross-section, the core including opposing side walls, joined to a web, the web of said core being perforated with a plurality of orifices substantially throughout the width and length of the web, said core defining with said side wall upper and lower longitudinally extending channels;
   b) a bundle of gas exchange hollow fibers of a composition suitable for gas exchange disposed substantially longitudinally in said upper channel, the fibers of which are layered outwardly from said core;
   c) a bundle of heat exchange hollow tubes impervious to liquid, said heat exchange bundle disposed substantially longitudinally in said lower channel, the tubes of which are layered outwardly from the core;
   d) first and second closure members joined to the opposing side wall at the outer edges of said channels and defining with said channels inlet and outlet manifold chamber space means outwardly of the outermost layers of said gas exchange fibers and outwardly of the outermost layers of said heat exchange tubes;
   e) the remote end regions of said tubes and said fibers being encapsulated with a polymeric material which bonds to said side walls and said first and second closure members to define a gas exchange cavity and a heat exchange cavity;
   f) outlet means in fluid communication with said outlet space means;
   g) inlet means in fluid communication with said inlet space means;
   h) said inlet and outlet chamber space means being constructed and arranged such that fluid flowing through said housing will flow in a direction generally transverse to the longitudinal direction of the gas exchange hollow fibers and heat exchange tubes;
   i) heat exchange fluid inlet means in fluid communication with the interior of the heat exchange hollow tubes at a first end thereof;
   j) heat exchange fluid outlet means in fluid communication with the interior of the heat exchange hollow tubes and disposed at the opposite end of the heat exchange tubes;

k) gas exchange inlet means for providing a gas inlet to the interior of the gas exchange hollow fibers at a first end thereof; and l) gas exchange outlet means for providing a gas outlet for the interior of the gas exchange hollow fibers, said outlet means being disposed at the opposite end of the hollow fibers from the inlet means.

2. The device of claim 1 wherein first and second diffuser plates are positioned respectively within said inlet and outlet manifold space means and in contact with and extending across the outermost layer of said hollow fibers and said tubes in each respective channel, said first and second diffuser plates each defining a plurality of orifices extending therethrough substantially throughout the diffuser plates, each of said diffuser plates being respectively spaced from said closure members.

3. The device of claim 2 wherein said diffuser plates are constructed and arranged such that the liquid to undergo gas exchange flowing through said device is distributed across substantially the entire surface of the first diffuser plate and the liquid to undergo gas exchange moves through said heat exchange bundle and said gas exchange bundle substantially in a planar flow until exiting through the second diffuser plate.

4. The device of claim 1 wherein a polymerized potting compound is positioned between at least a portion of the side walls of the core intermediate the ends thereof and the gas exchange hollow fibers so as to minimize channeling of bloods between said side walls and the gas exchange hollow fibers.

5. The device of claim 1 wherein a polymerized potting compound is positioned between at least a portion of the side walls of the core intermediate the ends thereof and the heat exchange tubes so as to minimize channeling of blood between said side walls and the heat exchange tubes.

6. The device of claim 1 wherein said gas exchange hollow fibers are arranged within said upper channel in layers of fibers such that each fiber is generally laid at an angle of between about 4 and 13 degrees from a longitudinal axis of said core and each succeeding fiber layer crosses the underlying fiber layer at an angle of between about 8 and 25 degrees with the cross-points of the fibers being offset from each other.

7. The device of claim 6 wherein the fibers are laid at and angle of about 9° from the side walls.

8. The device of claim 6 wherein said hollow fibers are packed within said upper channel to a pack density of between about 50 and about 55%.

9. The device of claim 1 wherein said heat exchange fluid inlet means and outlet means each comprise separate manifolds providing fluid communication to the lumens of the heat exchange hollow tubes and wherein said gas exchange inlet means and outlet means each comprise separate manifolds providing fluid communication to the lumens of the gas exchange hollow fibers, said heat exchange fluid manifolds and gas exchange manifolds being constructed and arranged such that neither fluid may flow between the gas exchange hollow fiber lumens and the heat exchange hollow tube lumens.

10. The device of claim 9 wherein the encapsulation of the end regions of said hollow fibers and said tubes, respectively, includes a unitary bonding to the encircling side walls and first and second closure members to give a gas-tight enclosure.

11. The device of claim 10 wherein the encapsulating polymeric material at each respective end region of said tubes and of said hollow fibers supports a resilient O-ring encircling said respective end region of said encapsulated fibers and said tubes and wherein said gas exchange inlet and outlet means and said heat exchange fluid inlet and outlet means each are constructed and arranged to sealingly engage the respective O-rings to provide a gas and liquid-tight seal.

12. A blood oxygenator comprising:
a) an elongated housing defining first and second opposite end openings, said housing having first and second opposing sides and a top and a bottom and first and second closure members over said end openings;
b) a bundle of hollow fibers for gas exchange being disposed inside said housing and having the ends of said fibers spaced from said end closure members, each fiber having an inlet and an outlet end, each of said fiber inlet ends and each of said fiber outlet ends being respectively in fluid communication with spaces defined by said first and second closure member and the ends of said fibers;
c) first and second sealant means encapsulating the exterior end portions of said hollow fibers adjacent the fiber inlets and outlets respectively and joined to the walls, top and bottom, to define a blood chamber cavity, the ends of the fibers being open to expose the interior of said fibers to the spaces defined respectively by said first and second end closure members;
d) blood inlet means communicating with said blood chamber cavity through said housing bottom;
e) blood outlet means communicating with said blood chamber cavity through said housing top;
f) gas inlet means communicating with the interior of said hollow fibers at the hollow fiber inlet ends;
g) gas outlet means communicating with the interior of said hollow fibers at the hollow fiber outlet ends; and
h) the blood chamber cavity including a space between the housing sides and the hollow fiber bundle therein, said space being substantially filled with a potting compound.

13. The blood oxyenator of claim 12 wherein each said sealant means includes a surface supporting a resilient O-ring encircling the perimeter thereof and wherein said gas inlet and said gas outlet means are each constructed and arranged to sealingly engage the respective O-rings.

14. The blood oxygenator of claim 12 wherein said hollow fibers are arranged within said housing in a migrating pattern of crossing layers of hollow fibers, said crossed layers of fibers thereby reinforcing each other against a tendency to move under the hydraulic pressure of flowing blood and wherein said hollow fibers are packed within said housing at a density of about 50 to about 55%.

15. A hollow fiber-type device having an integral heat exchanger, said device comprising:
a) an oxygenator section, said oxygenator section including:
an elongated rigid core of H-shaped cross section having a longitudinal axis and defining an upper and lower longitudinally extending groove in said core, the core including a center divider between opposing side walls of the core, which together define said grooves, said center divider being perforated with a plurality of orifices substantially throughout the width and length of the center divider, a plurality of oxygenation hollow fibers arranged longitudinally in said upper groove, said fibers being arranged in layers successively upward from the core, each fiber crossing over the next at an angle of from about 4 to about 13 degrees from the longitudinal axis of the core;

first and second walls in supportive relationship to the respective ends of said hollow fibers at the remote ends thereof with said ends of said hollow fibers left open to the interiors thereof, said first and second walls being secured to said core;

first and second closure means defining with said first and second walls, respectively, first and second manifold chamber space means at the inlet and outlet ends of said fibers;

oxygen inlet means communicating with the first manifold chamber space means;

gas outlet means communicating with the second manifold chamber space means;

a first cover means enclosing said upper groove side walls and end walls said first cover means defining an outlet chamber above the uppermost layer of hollow fibers, said first cover means further including an outlet plate constructed and arranged so as to contact substantially the entire uppermost layer of hollow fibers, said outlet plate including a plurality of orifices substantially throughout the width and length of the outlet plate, said first cover means and outlet plate being constructed and arranged such that fluid within said outlet chamber between the first cover means and outlet plate may pass from said hollow fibers only through said outlet plate orifices;

a blood outlet passage provided in the first cover means, said passage being constructed and arranged so as to allow passage of blood from said outlet chamber to the exterior of said device;

said hollow fibers within the space defined by said core, first and second walls and inlet plate being packed to a density of about 50 to about 55 percent;

b) a heat exchanger section, said heat exchanger section including a plurality of polymeric hollow tubes arranged side by side longitudinally in said lower groove of said elongated rigid core in layers successively downward from said core;

third and fourth walls in supportive relationship to the respective ends of said heat exchanger hollow tubes at the remote ends thereof, with said end portions of said hollow tubes left open to the interior thereof, said third and fourth walls being secured to said core;

third and fourth closure means defining with said third and fourth walls, respectively, first and second heat exchanger manifold chambers at the inlet and outlet ends of said heat exchanger tubes;

a heat exchange medium inlet means communicating with the first heat exchanger manifold chamber;

a heat exchange medium outlet means communicating with the second heat exchanger manifold chamber;

a second cover means enclosing said lower groove side walls and third and fourth walls, said second cover means defining an inlet chamber between the lowermost layer of heat exchanger hollow tubes from said center divider, said second cover means further including an inlet plate constructed and arranged so as to contact substantially the entire lowermost heat exchanger hollow tube layer, said inlet plate including a plurality of orifices, substantially throughout the width and length of the inlet plate, said second cover means and inlet plate being constructed and arranged such that fluid surrounding said heat exchanger hollow tubes may pass into said inlet chamber only through said inlet plate orifices; and a blood inlet passage provided in the second cover means, said inlet passage being constructed and arranged so as to allow passage of blood into said inlet chamber.

16. The hollow fiber-type device of claim 15 wherein said first and second walls each include a surface encircling the perimeter thereof supporting a resilient O-ring and wherein said first and second closure means at said oxygen inlet means and said gas outlet means, respectively, are constructed and arranged to sealingly engage the respective first and second wall O-rings.

17. The hollow fiber-type device of claim 16 wherein third and fourth walls each include a surface encircling the perimeter thereof supporting a resilient O-ring and wherein said third and fourth closure means, respectively, are constructed and arranged to sealingly engage the respective third and fourth wall O-rings.

18. The hollow fiber-type device of claim 15 wherein said gas exchange hollow fibers are arranged such that each succeeding layer of fibers generally crisscrosses the next adjacent layer of fibers at an angle of about 9 degrees from the longitudinal axis of the core.

19. The hollow fiber-type device of claim 15 wherein a potting compound is located between the side walls of the core and the oxygenator hollow fibers immediately adjacent the side walls so as to substantially fill all void space therebetween.

20. The hollow fiber-type device of claim 15 wherein said core, all of the walls and the inlet and outlet plates are formed from a biocompatible polycarbonate polymer.

21. The hollow fiber-type device of claim 15 wherein said inlet plate is held in a spaced relationship from said second cover means by a plurality of spacing nodes and said outlet plate is held in a spaced relationship from said first cover means by a plurality of spacing nodes.

* * * * *